United States Patent [19]
Washburn et al.

[11] Patent Number: 5,510,342
[45] Date of Patent: Apr. 23, 1996

[54] METHOD OF LOWERING CHOLESTEROL

[75] Inventors: Scott A. Washburn; Thomas B. Clarkson, both of Forsyth, N.C.; Steven J. Adelman, Montgomery, Pa.; Michael S. Dey, Grand Isle, Vt.

[73] Assignees: American Home Products Corporation, Madison, N.J.; Wake Forest University, Winston-Salem, N.C.

[21] Appl. No.: 404,943

[22] Filed: Mar. 15, 1995

Related U.S. Application Data

[63] Continuation of Ser. No. 970,348, Nov. 2, 1992, abandoned.

[51] Int. Cl.$^6$ .................................................. A61K 31/56
[52] U.S. Cl. .................... 514/179; 552/625; 552/626
[58] Field of Search .................................. 514/178–182

[56] References Cited

U.S. PATENT DOCUMENTS

| | | | |
|---|---|---|---|
| 4,154,820 | 5/1979 | Simoons | 424/175 |
| 4,826,831 | 5/1989 | Plunkett | 514/170 |
| 4,894,373 | 1/1990 | Young | 514/239.2 |

OTHER PUBLICATIONS

Lobo, R. A., Fertility and Sterility 49:234 (1988).
Walsh, B. W., The New England Journal of Medicine 325:1196 (1991).
Novakovic, J., Journal of Pharmaceutical & Biomedical Anal. 8:253 (1990).
Glen, W. L., Nature 177: 753 (1956).
Howard, R. P., Arch. Intern. Med. 128:229 (1971).
Stern, M. D., Maturitas 4:333 (1982).
Stern, M. D., Endometrial Cancer, Brush, ed., 309 (1978).
Grant, G. A., Recent Prog. Horm. Res. 5: 307 (1950).
Bhavnani, B. R., Steroids 56:201 (1991).
Bhavnani, B. R. J. Clin. Endocrin. Metab. 56: 1048 (1983).
Bhavnani, B. R., Endocrin. 108:232 (1981).
Lyman, G. W., Chrom. 14: 234 (1982).
Ross, R. K., Am. J. Obstet. Gynecol. 160: 1301 (1989).
Barrett–Connor, E., JAMA 261: 2095 (1989).
Lobo, R. A., Obstet. Gynecol. 75: 18S (1990).
Stampfer, M. J., N. E. J. Med. 313: 1044 (1985).
Barrett–Connor, E., Annu. Rev. Med. 43: 239 (1992).
Barrett–Connor, E., JAMA 265:1861 (1991).
Bhavnani, B. R., J. Steroid Biochem. 17: 217 (1982).
Levy, R., Am. Heart J. 110: 1116 (1985).
Ross, R., New Eng. J. Med. 295: 369 (1977).
Ross, R., New Eng. J. Med. 314: 488 (1986).
Manderson, J. A., Arteriosclerosis 9: 289 (1989).
Clowes, A. W., Circ. Res. 56: 139 (1985).
Clowes, W. W., J. Cardiovas. Pharm. 14 (Suppl 6): S12 (1989).
Barrett–Connor, E., JAMA 265: (1991).
Chao, Y–S., J. Biol. Chem. 254: 11360 (1979).
Kovanen, P. T., J. Biol. Chem. 254: 11367 (1979).
Windler E. E. T., J. Biol. Chem., 255: 10464 (1980).
Utian, W. H., Obstet. Gynecol. Surv. 32: 193 (1977).
ACOG Technical Bulletin 93: 1 (1986).
Hammond, C. B., Fertil. Steril. 37: 5 (1982).
Whitehead, M. I., Am. J. Obstet. Gynecol. 142: 791 (1982).
Gambrell, R. D., South Med. J. 71: 1280 (1978).
McDonald T. W., Am. J. Obstet. Gynecol. 127: 572 (1977).
Whitehead, M. I., J. R. Soc. Med. 72: 322 (1979).

*Primary Examiner*—Shep K. Rose
*Attorney, Agent, or Firm*—Darby & Darby

[57] ABSTRACT

This invention provides a method of lowering cholesterol and blood lipid levels, preventing hypercholesterolemia, hyperlipidemia, cardiovascular disease, atherosclerosis, and peripheral vascular disease comprising administering an effective amount of 17α-dihydroequilenin or a mammalian metabolic conjugate thereof to a mammal in need thereof.

8 Claims, No Drawings

METHOD OF LOWERING CHOLESTEROL

This is a continuation of application Ser. No. 07/970,348, filed Nov. 2, 1992, now abandoned.

BACKGROUND OF THE INVENTION

This invention relates to a method of using 17α-dihydroequilenin to lower cholesterol and blood lipid levels and for preventing hypercholesterolemia hyperlipidemia, cardiovascular disease (CVD), atherosclerosis, and peripheral vascular disease.

Coronary artery disease, the primary form of CVD, is the major cause of death in the United States today, responsible for over 550,000 deaths per year. Cerebrovascular disease is the third leading cause of death in the United States. The etiology of both coronary artery and cerebrovascular diseases is attributed to atherosclerosis. Through its clinical manifestations, atherosclerosis is the major cause of the more than one million heart attacks and approximately 400,000 strokes that occur each year. In addition to the high morbidity and mortality associated with atherosclerosis, it has been estimated that atherosclerosis has cost the United States' economy over $80 billion each year in lost wages, lost productivity, and medical care costs [Levy, R., Am. Heart J. 110:1116 (1985)]. A substantial body of evidence has established a causal relationship between hypercholesterolemia and premature atherosclerosis; the higher the levels of plasma cholesterol, the greater the risk of subsequent heart attack. [Steinberg, D., JAMA 264:3047 (1991); Lipid Research Clinics Program, JAMA 251:351 (1984); Rifkind, B., Am. J. Cardiol. 54: 30C (1984)].

In the chain of events leading to atherosclerosis, it is believed that the initiating event is the formation of "fatty streaks" in carotid, coronary, and cerebral arteries, and in the aorta. These lesions comprise of fatty deposits of cholesterol and cholesteryl ester that are found principally within the smooth muscle cells and macrophages of the intimal layer [Ross, R., New Eng. J. Med. 295:369 (1977)]. The migration and proliferation of vascular smooth muscle cells play a crucial role in the pathogenesis of atherosclerosis following the initial deposition of lipid. Under normal circumstances, the cells of the arterial wall can be looked at as being under stringent negative control and in a quiescent non-proliferating state, probably the consequence of contact with their specialized extracellular matrix. Desquamation or injury of the endothelium, resulting in exposure of and possible disruption of the integrity of the extracellular matrix surrounding the cells, leads to 1) recruitment of circulating monocytes and their differentiation to macrophages, 2) accumulation of lipid in macrophages and smooth muscle cells [Ross, R., New Eng. J. Med. 314:488 (1986)], 3) a shift in smooth muscle phenotype from a quiescent, contractile state to a migrating, proliferative form [Manderson, J. A., Arterio 9:289 (1989)], 4) eventual migration of transformed smooth muscle cells from the medial layer to the sub-lesion intimal layer [Clowes, A. W., Circ. Res. 56:139 (1985)] and 5) subsequent massive proliferation of the intimal smooth muscle layer resulting in arterial luminal blockage [Clowes, A. W., J. Cardiovas. Pharm. 14 (Suppl 6): S12 (1989)].

Several risk factors have been identified in individuals who develop atherosclerosis. It can be inferred that persons with at least one risk factor will be at greater risk of developing atherosclerosis than persons with no risk factors. Persons with multiple risk factors are even more susceptible. The risk factors include hyperlipidemia (hypercholesterolemia and/or hypertriglyceridemia), hyperglycemia, diabetes, hypertension, obesity, cigarette smoking, familial hyperlipoproteinemia, and aging. Of these factors, it is well established that elevated serum cholesterol levels is the one of the most important contributing factors leading to the development or progression of atherosclerosis.

Peri- and post-menopausal women are one particular group of aging persons at risk for developing coronary heart disease. Since the 1950s, it has been observed that premenopausal women are protected from coronary heart disease. These observations prompted several animal studies which demonstrated that the administration of estrogens to animals fed a high fat diet prevented dietary-induced coronary atherosclerosis. [Barrett-Connor, E., JAMA 265:(1991)]. One of the mechanisms by which estrogen is thought to be protective against atherosclerotic coronary heart disease is by lowering total plasma cholesterol (TPC) through induction of increased catabolism and excretion of low density lipoprotein (LDL) particles into bile by the liver. This increased LDL catabolism and excretion may be a result of an estrogen dependent increase in low density lipoprotein receptors in the liver, as has been demonstrated in rats given large pharmacologic doses of 17α-ethinyl estradiol. [Chao, Y-S., J. Biol. Chem. 254:11360 (1979); Kovanen, P. T., J. Biol. Chem. 254:11367 (1979); Windler E. E. T. , J. Biol. Chem., 255:10464 (1980)]. Women who receive postmenopausal estrogen replacement therapy (ERT) have been shown to benefit from a fifty to seventy percent reduction in risk from atherosclerotic related coronary heart disease. [Stampfer, M. L., N. Engl. J. Med. 313:1044 (1985)]. The mortality from CVD is 63% lower and the rate of mortality from myocardial infarction is between 2.3 and 2.7 times lower in estrogen-treated women compared with untreated climacteric women.

While the benefits of ERT in postmenopausal women are substantial, an association has been established between the use of unopposed ERT (estrogen therapy without concomitant progestin administration) and endometrial hyperplasia, thereby increasing the risk of endometrial carcinoma. [Utian, W. H., Obstet. Gynecol. Surv. 32:193 (1977); ACOG Technical Bulletin 93:1 (1986); Hammond, C. B., Fertil. Steril. 37:5 (1982); Whitehead, M. I., Am. J. Obstet. Gynecol. 142:791 (1982); Gambrell, R. D., South Med. J. 71:1280 (1978); McDonald T. W., Am. J. Obstet. Gynecol. 127:572 (1977)]. To reduce or entirely eliminate the risk of endometrial adenocarcinoma resulting from ERT while maintaining the benefits of ERT, it has been shown that progestins can be administered concomitant with the estrogen during the last 10–14 days of each estrogen cycle. [Whitehead, M. I., J. R. Soc. Med. 72:322 (1979); Whitehead, M. I., Semin. Reprod. Endocrin. 1:41 (1983); Barrett-Connor, E., Annu. Rev. Med. 43:239 (1992)].

The isolation of 17α-dihydroequilenin from pregnant mare's urine was reported in 1956. [Glen, W. L., Nature 177:753 (1956)]. 17α-Dihydroequilenin sulfate is a 1% by weight component of PREMARIN® conjugated estrogens (PREMARIN is a Registered Trademark of Wyeth-Ayerst), a drug commonly prescribed as ERT in postmenopausal women. There have been several reports of the relative estrogenicity of various estrogens to determine if they have differential effects on menopausal vasomotor symptoms, urinary gonadotropin levels, plasma lipid and lipoprotein metabolism and hepatic globulin synthesis compared to uterine response. Two studies showed that 17α-dihydroequilenin had essentially no stimulatory effect on uterine weight or maturation of vaginal cytology in the rat model and did not suppress urinary gonadotropins in postmenopausal women. Estrogenic activity was nil to minimal. [Howard, et al., Arch Int. Med. 128:229 (1971); Stern, Maturitas 4:333 (1982). Neither study suggested the use of 17α-dihydroequilenin in lowering cholesterol.

DESCRIPTION OF THE INVENTION

This invention provides a method of lowering cholesterol in a mammal in need thereof which comprises administering a cholesterol lowering effective amount of 17α-dihydroequilenin or a mammalian metabolic conjugate to a mammal in need thereof orally, parenterally, transdermally, rectally, intravaginally, intranasally, or intrabronchially. This invention also provides a method of preventing hypercholesterolemia and hyperlipidemia in a susceptible mammal. This invention additionally provides a method of lowering blood lipid levels in a hyperlipidemic mammal. Particular lipids that are lowered include triglycerides, cholesterol, LDL, and combinations thereof. By virtue of the ability of 17α-dihydroequilenin to lower cholesterol, this invention additionally provides a method of preventing cardiovascular disease, atherosclerosis, and peripheral vascular disease. This invention further provides pharmaceutical compositions for the treatment or prevention of the above conditions comprising an effective amount of 17α-dihydroequilenin or a mammalian metabolic conjugate thereof and a pharmaceutical carder.

This invention is useful in lowering cholesterol in both male and female mammals that have elevated cholestesterol levels, and in preventing hypercholesterolemia and hyperlipidemia in mammals that are susceptible to such conditions. In particular, susceptible mammals include, but are not limited to, those mammals with a familial history of elevated cholesterol levels, peri- or post-menopausal females, surgically or chemically induced estrogen deficient females, the aged, those with hyperglycemia, diabetes, hypertension, and obesity, and cigarette smokers. Other populations of mammals that are susceptible to the risk of developing elevated cholesterol levels will be apparent to one skilled in the art.

The mammalian metabolic conjugates are sulfates and glucuronides of 17α-dihydroequilenin, where 17α-dihydroequilenin can either be in the form of a mono- or di-conjugate. In addition, it is also contemplated that any derivative of 17α-dihydroequilenin that forms 17α-dihydroequilenin or a conjugate thereof in vivo will also be useful in preventing or treating the conditions described above.

17α-Dihydroequilenin is commercially available and the conjugates are either commercially available or can be prepared by using standard chemical methodology.

The ability of 17α-dihydroequilenin to lower cholesterol was established in an in vivo standard pharmacological test procedure which evaluated the effect of 17α-dihydroequilenin on cholesterol levels in oophrectomized rats. Uterine weight and triglyceride levels were also measured. Estrone sulfate, 17α-estradiol sulfate, and PREMARIN conjugated estrogens were also evaluated for the purpose of comparison. Estrone sulfate is approximately 25 times more estrogenic than 17α-dihydroequilenin sulfate. The procedure used and results obtained are briefly described below.

Nine week old virgin female Fischer 344 rats were allowed to have free access to food and water in a single cage housing setup. The animals were exposed to 12 hour light and 12 hour dark cycles and had body weight determined weekly. The rats were divided into 5 treatment groups receiving: no treatment (control), 17α-dihydroequilenin sulfate, PREMARIN conjugated estrogens, estrone sulfate, and 17α-estradiol sulfate. After acclimatization to single cage housing all of the animals were anesthetized with ketamine (100 mg/kg IM) and xylazine (12 mg/kg IM) and bled via ocular sinus venipuncture for determination of total plasma cholesterol [Auerbach, B. J., J. Lipid Res., 30:738–42 (1990)]. During the same anesthesia, all the animals were oophorectomized. Pretreatment cholesterol levels were unable to be obtained due to hemolysis. Each group received the designated treatment for a 120-day period, after which total plasma cholesterol levels were measured and uterine weight determined.

The following table shows the results that were obtained.

TABLE 1

EFFECT OF 17α-DIHYDROEQUILENIN SULFATE ON CHOLESTEROL LEVELS IN OVARIECTOMIZED FEMALE RATS

| Group | n | Total Plasma Cholesterol (mg/dL ± SEM) | Uterine Weight (mg ± SEM) |
|---|---|---|---|
| Control | 37 | 90.44 ± 1.06 | 124.63 ± 12.02 |
| 17α-Dihydroequilenin sulfate | | | |
| 0.156 mg/day | 8 | 35.02 ± 3.44* | 162.34 ± 15.83 |
| 0.078 mg/day | 10 | 32.49 ± 1.08* | 125.38 ± 11.91 |
| 0.0156 mg/day | 9 | 71.55 ± 5.16* | 145.84 ± 18.87 |
| PREMARIN conjugated estrogens | | | |
| 0.01 mg/day | 10 | 76.07 ± 2.40* | 243.34 ± 7.15* |
| 0.005 mg/day | 9 | 90.51 ± 4.36 | 141.02 ± 12.43 |
| Estrone Sulfate | | | |
| 0.006 mg/day | 9 | 83.70 ± 2.06 | 376.1 ± 9.36* |
| 0.003 mg/day | 10 | 70.73 ± 3.17* | 249.02 ± 6.34* |
| 0.0006 mg/day | 10 | 88.29 ± 3.31 | 188.02 ± 10.19 |
| 17α-Estradiol sulfate | | | |
| 0.054 mg/day | 10 | 81.86 ± 5.85 | 162.93 ± 21.50 |
| 0.027 mg/day | 10 | 89.88 ± 4.73 | 133.09 ± 6.87 |
| 0.0054 mg/day | 10 | 86.25 ± 2.92 | 163.41 ± 32.36 |

*Statistically significant ($p < 0.01$) difference from control.

The results obtained in the standard pharmacological test procedure, as shown in Tables 1, demonstrate that 17α-dihydroequilenin is useful in lowering cholesterol levels. Total plasma cholesterol levels were significantly ($p<0.01$) decreased following treatment with 17α-dihydroequilenin at all dose levels evaluated. This result is unexpected, because of the lack of estrogenicity of 17α-dihydroequilenin. Uterine weight was not significantly increased following treatment with 17α-dihydroequilenin, confirming the lack of estrogenicity. Levels of plasma cholesterol were also reduced to a greater extent with 17α-dihydroequilenin than with the estrogenic treatment regimens (PREMARIN conjugated estrogens, estrone sulfate, and 17α-estradiol sulfate), which have been previously been shown to effectively reduce cholesterol levels [Ross, R., Am. J. Obstet. Gynecol. 160:1301 (1989); Barrett-Connor, E., JAMA 261:2095 (1989); Lobo, R., Obstet. Gynecol. 75: 18S (1990)].

The cholesterol lowering ability of 17α-dihydroequilenin was also demonstrated in three standard pharmacological test procedures in which triglyceride levels, total cholesterol levels, HDL levels, and levels of the atherogenic LDL/VLDL subfractions were measured. These test procedures used a shorter period of drug administration (4 days), and evaluated 17α-dihydroequilenin in both ovariectomized female rats as well as normal male rats. The differences from the procedure used above, and the results obtained are described below.

The following results were obtained in 4–6 week old ovariectomized Sprague-Dawley rats that were fed a normal rat chow diet supplemented with doses of drug for 4 days. Eight (8) rats in each group were either given no treatment (control group) or were treated with 17α-dihydroequilenin sulfate or 17α-estradiol sulfate. The rats were allowed to eat ad. lib. and were sacrificed on the fifth day. Drug was administered by gavage once daily. No food was administered on the fifth day. Plasma was collected and the lipid levels were determined by autoanalyzer.

The following results were obtained in ovariectomized rats that were fed a normal rat chow diet supplemented with doses of drug for 4 days. Eight (8) rats in each group were either given no treatment (control group) or were treated with 17α-dihydroequilenin sulfate or 17α-estradiol sulfate. The rats were allowed to eat ad. lib. and were sacrificed on the fifth day. As the compounds tested were admixed in the diet, the doses shown in the table below represent an approximate daily dose administered. No food was administered on the fifth day. Plasma was collected and the lipid levels were determined by autoanalyzer.

TABLE 2

EFFECT OF 17α-DIHYDROEQUILENIN SULFATE ON CHOLESTEROL LEVELS IN OVARIECTOMIZED FEMALE RATS

| Group | Triglycerides (mg/dL) | Total Cholesterol (mg/dL) | HDL (mg/dL) | LDL + VLDL (mg/dL) | Uterine Weight (mg) |
|---|---|---|---|---|---|
| Control | 40.4 | 62.9 | 34.4 | 28.5 | 110 |
| 17α-Dihydroequilenin sulfate | | | | | |
| 1.25 mg/kg | 43.2 | 34.0* | 20.2* | 13.8* | 120 |
| 0.625 mg/kg | 30.4* | 48.6* | 30.0 | 18.7* | 107 |
| 0.313 mg/kg | 29.3* | 58.2 | 34.1 | 24.1* | 103 |
| 0.156 mg/kg | 28.8* | 66.1 | 39.2 | 27.0 | 108 |
| 0.078 mg/kg | 32.6* | 69.5 | 39.6 | 29.9 | 108 |
| 17α-Estradiol sulfate | | | | | |
| 0.05 mg/kg | 41.8 | 63.5 | 35.4 | 28.1 | 124 |

*Statistically significant (p < 0.05) difference from control.

The following results were obtained in 4–6 week old normal male Sprague-Dawley rats that were fed a normal rat chow diet supplemented with doses of drug for 4 days. Eight (8) rats in each group were either given no treatment (control group) or were treated with 17α-dihydroequilenin sulfate or 17α-estradiol sulfate. The rats were allowed to eat ad. lib. and were sacrificed on the fifth day. Drug was administered by gavage once daily for 4 days. No food was administered on the fifth day. Plasma was collected and the lipid levels were determined by autoanalyzer.

TABLE 3

EFFECT OF 17α-DIHYDROEQUILENIN SULFATE ON CHOLESTEROL LEVELS IN NORMAL MALE RATS

| Group | Triglycerides (mg/dL) | Total Cholesterol (mg/dL) | HDL (mg/dL) | LDL + VLDL (mg/dL) | Testicular Wt. (g) |
|---|---|---|---|---|---|
| Control | 31.9 | 57.3 | 32.8 | 24.5 | 2.03 |
| 17α-Dihydroequilenin sulfate | | | | | |
| 1.25 mg/kg | 30.2 | 42.9* | 23.6* | 19.3 | 2.08 |
| 0.625 mg/kg | 29.4 | 50.5 | 30.5 | 20.0 | 2.10 |
| 0.313 mg/kg | 29.2 | 54.1 | 31.3 | 22.8 | 2.01 |
| 0.156 mg/kg | 25.4 | 50.2 | 30.6 | 19.5 | 2.08 |
| 0.078 mg/kg | 31.7 | 54.1 | 34.5 | 19.5 | 1.90 |
| 17α-Estradiol sulfate | | | | | |
| 0.05 mg/kg | 26.5 | 51.8 | 29.3 | 22.5 | 2.04 |

*Statistically significant (p < 0.05) difference from control.

As shown in Tables 2 and 3, 17α-dihydroequilenin lowered total cholesterol levels and also lowered levels of the atherogenic LDL/VLDL cholesterol subfractions in both female as well as in male rats.

TABLE 4

EFFECT OF 17α-DIHYDROEQUILENIN SULFATE ON CHOLESTEROL LEVELS IN OVARIECTOMIZED FEMALE RATS

| Group | Triglycerides (mg/dL) | Total Cholesterol (mg/dL) | HDL (mg/dL) | LDL + VLDL (mg/dL) | Uterine Weight (mg) |
|---|---|---|---|---|---|
| Control | 51.8 | 74.4 | 44.1 | 30.3 | 170 |
| 17α-Dihydroequilenin sulfate | | | | | |
| 0.625 mg/kg | 27.0* | 16.5* | 10.7* | 5.8* | 143 |
| 0.312 mg/kg | 34.3* | 30.4* | 20.8* | 9.6* | 140 |
| 0.0625 mg/kg | 37.5* | 52.1* | 34.6* | 17.5* | 127* |
| 17α-Estradiol sulfate | | | | | |
| 0.2 mg/kg | 38.9* | 62.1* | 40.3 | 21.8* | 179 |

*Statistically significant (p < 0.05) difference from control.

As shown in Table 4, 17α-dihydroequilenin significantly ($p<0.05$) lowered triglyceride levels, total cholesterol levels, HDL levels and LDL/VLDL levels. Considering the dramatic decrease in total cholesterol and LDL/VLDL levels, it is not surprising that the HDL levels were also reduced, as rats are an HDL-rich species. No uterotrophic effect was observed. Additionally, the cholesterol lowering effect was much greater when 17α-dihydroequilenin was administered throughout the day (Table 4) than when 17α-dihydroequilenin was administered only once daily (Tables 2 and 3). The total amount of 17α-dihydroequilenin administered to each dose level group was the same, indicating that multiple small-dose administrations during the day may produce more favorable results than once daily administration.

The results of these in vivo standard pharmacological test procedures demonstrate the cholesterol lowering ability of 17α-dihydroequilenin. Based on the results obtained, 17α-dihydroequilenin is useful in lowering cholesterol levels in a mammal in need thereof and in preventing hypercholesterolemia and hyperlipidemia in a susceptible mammal. By virtue of the ability of 17α-dihydroequilenin to lower cholesterol, 17α-dihydroequilenin is also useful in preventing cardiovascular disease, atherosclerosis, and peripheral vascular disease.

When 17α-dihydroequilenin is employed as described in this invention, it can be formulated into oral dosage forms such as tablets, capsules and the like. 17α-Dihydroequilenin can be administered alone or by combining it with conventional carriers, such as magnesium stearate, microcrystalline cellulose, talc, sugar, lactose, dextrin, starch, gelatin, tragacanth, methylcellulose, sodium carboxymethylcellulose, low melting wax, cocoa butter and the like. Diluents, flavoring agents, solubilizers, stabilizers, lubricants, suspending agents, binders, tablet-disintegrating agents and the like may be employed. 17α-Dihydroequilenin may be encapsulated with or without other carriers. In all cases, the proportion of active ingredients in said compositions both solid and liquid will be at least to impart the desired activity thereto on oral administration. 17α-Dihydroequilenin may also be injected parenterally, in which case it is used in the form of a sterile solution containing other solutes, for example, enough saline or glucose to make the solution isotonic.

17α-Dihydroequilenin also may be administered rectally in the form of a conventional suppository. For administration by intranasal or intrabronchial inhalation or insufflation, 17α-dihydroequilenin may be formulated into an aqueous or partially aqueous solution or a powdered aerosol, which can then be utilized in the form of an aerosol. 17α-Dihydroequilenin may also be administered transdermally through the use of a transdermal patch containing the active compound and a carrier that is inert to the active compound, is nontoxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 µg/kg–100 mg/kg, preferably between 1 µg/kg–50 mg/kg, and more preferably between 5 µg/kg–25 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. In general, 17α-dihydroequilenin is most desirably administered at a concentration that will generally afford effective results without causing any harmful or deleterious side effects, and can be administered either as a single unit conventional or sustained release dose, or if desired, the dosage may be divided into convenient subunits administered at suitable times throughout the day.

The above described formulations and dosages are also applicable when 17α-dihydroequilenin is administered in the form of a mammalian metabolic conjugate.

What is claimed is:

1. A method of lowering cholesterol levels in a mammal, consisting essentially of administering to a mammal in need of lowered cholesterol levels, a cholesterol lowering effective amount of 17α-dihydroequilenin or a mammalian metabolic conjugate thereof as said cholesterol lowering ingredient, by a route of administration selected from the group consisting of oral, parental, transdermal, rectal, intravaginal, intranasal and intrabronchial administration.

2. The method according to claim 1, wherein the administered compound is 17α-dihydroequilenin surfate.

3. A method of preventing hypercholesterolemia in a hypercholesterolemically-susceptible mammal, consisting essentially of administering to a hypercholesterolemically susceptible mammal an antihypercholesterolemic effective amount of 17α-dihydroequilenin or a mammalian metabolic conjugate thereof as antihypercholesterolemic ingredient, by a route of administration selected from the group consisting of oral, parental, transdermal, rectal, intravaginal, intranasal and intrabronchial administration.

4. The method according to claim 3, wherein the administered compound is 17α-dihydroequilenin sulfate.

5. A method of lowering blood lipid levels in a mammal, consisting essentially of administering to a mammal in need of lowered blood lipid levels a lipid lowering effective amount of 17α-dihydroequilenin or a mammalian metabolic conjugate thereof as said lipid lowering ingredient, by a route of administration selected from the group consisting of oral parental, transdermal, rectal, intravaginal, intranasal and intrabronchial administration and wherein said blood lipid is selected from the group consisting of a triglyceride, cholesterol, LDL, and mixtures thereof.

6. The method according to claim 5, wherein the administered compound is 17α-dihydroequilenin sulfate.

7. A method of preventing hyperlipidemia in a susceptible mammal, consisting essentially of administering to a hyperlipidemically-susceptible mammal an antihyperlipidemic effective amount of 17α-dihydroequilenin or a mammalian metabolic conjugate thereof as said antihyperlipidemic ingredient, by a route of administration selected from the group consisting of oral, parental, transdermal, rectal, intravaginal, intranasal and intrabronchial administration.

8. The method according to claim 7, wherein the administered compound is 17α-dihydroequilenin sulfate.

* * * * *